`United States Patent` [19]

Linder et al.

[11] 3,962,342

[45] June 8, 1976

[54] BROMINATION PROCESS

[75] Inventors: Jerome Linder, Westfield; William J. Houlihan, Mountain Lakes, both of N.J.

[73] Assignee: Sandoz, Inc., E. Hanover, N.J.

[22] Filed: Mar. 24, 1975

[21] Appl. No.: 561,485

[52] U.S. Cl. ............................................. 260/592
[51] Int. Cl.² ..................................... C07C 49/80
[58] Field of Search ................................. 260/592

[56] References Cited
UNITED STATES PATENTS 3,870,751   3/1975   Houlihan et al. .................. 260/592

OTHER PUBLICATIONS

Beaupere et al., Chem. Abstracts 79 4753b (1973).

Primary Examiner—D. Horwitz
Attorney, Agent, or Firm—Gerald D. Sharkin; Robert S. Honor

[57] ABSTRACT

The α-bromo-substituted or unsubstituted-4-pivaloyl toluenes, e.g., α-bromo-4-pivaloyl toluene, are prepared by bromination of a corresponding p-pivaloyl toluene with liquid bromine at a temperature of at least 100°C.

5 Claims, No Drawings

BROMINATION PROCESS

This invention relates to α-bromo-substituted or unsubstituted-4-pivaloyl toluenes. In particular, it relates to a process for preparing α-bromo-4-pivaloyl toluenes, which are useful as intermediates in the preparation of compounds having pharmaceutical activity.

In the conventional method of carrying out the bromination of p-pivaloyl toluenes, a brominating agent is employed in the presence of an inert organic solvent and a free radical initiator, and certain amounts of by-product are obtained. If a free radical initiator is not employed, low yields are obtained at moderate temperatures; and if a free radical initiator is employed, the reaction takes extended periods of time, on the order of several hours, in order to obtain reasonable yields.

It has now been found that when the bromination process is carried out by adding liquid bromine without either an inert organic solvent or free radical initiator at a temperature of at least 100°C., the amount of undesirable by-product is significantly decreased, whereas the purity of the desired α-bromo-4-pivaloyl toluene is significantly increased, the latter being a totally unexpected result, and the time required to run the reaction is minimal.

The present invention, accordingly, provides an improved process for preparing compounds of the formula:

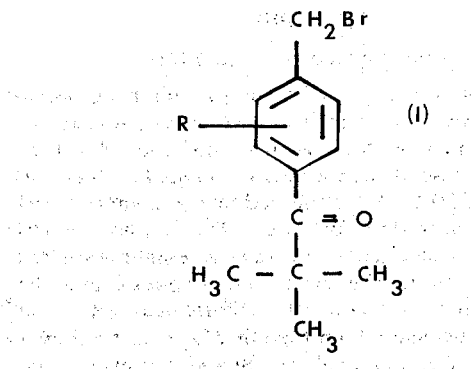

where
R represents hydrogen or halo having an atomic weight of about 19 to 36,
which comprises treating a compound of the formula:

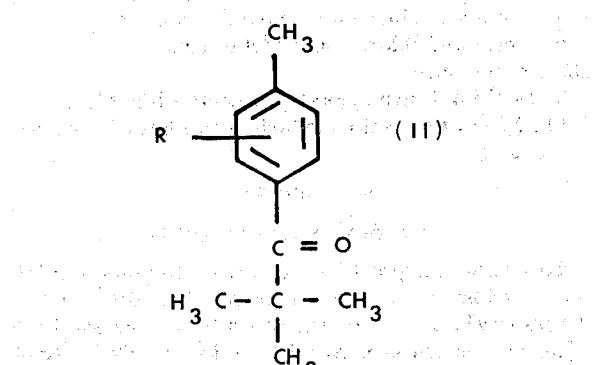

where
R is as defined above, with liquid bromine, the improvement comprising the addition of liquid bromine without an inert organic solvent or a free radical initiator. The mole ratio of liquid bromine to a compound of the formula (II) is 0.5–1:1. The temperature of the reaction is critical in that the bromination process should be carried out at a temperature of at least 100°C., preferably from about 108° to 175°C., especially from about 115° to 150°C. It is also preferred that the liquid bromine be added cautiously, e.g., dropwise, over a period of 10 minutes to 1 hour, preferably 10 to 30 minutes. After the addition of the liquid bromine is completed, the reaction mixture is preferably stirred for an additional 10 minutes to 2 hours, in particular, 10 minutes to 1 hour, especially 10 minutes to 30 minutes. The compounds of formula (I) are liquids.

The compounds of formula (I) are used to prepare substituted or unsubstituted-4-pivaloylphenyl acetonitriles in accordance with the following reaction scheme:

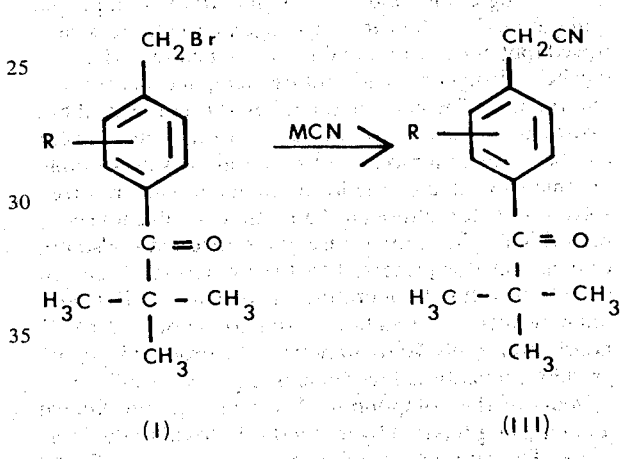

where
M represents an alkali metal, preferably sodium or potassium, and
R is as defined above.

The compounds of formula (III) are prepared by treating compounds of formula (I) with an alkali metal cyanide such as sodium cyanide, potassium cyanide, and the like, preferably potassium cyanide, in the presence of an aqueous organic solvent. The preferred solvents are the aqueous lower alkanols such as water and methanol, ethanol and the like, and water-dioxane, although anhydrous dimethylsulfoxide can also be employed. The temperature of the reaction is not critical but it is preferred that the process be carried out at a temperature between about 40° to 120°C., especially the reflux temperature of the system. For optimum results, the reaction is run for about 1 to 10 hours, preferably 3 to 5 hours. The product is recovered by conventional techniques, e.g., evaporation.

The compounds of formula (III) are useful in the preparation of substituted or unsubstituted-4-pivaloylphenyl acetic acids in accordance with the following reaction scheme:

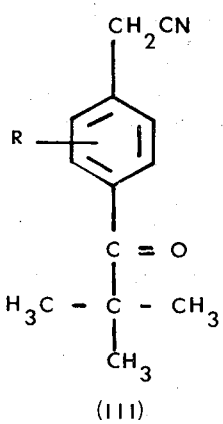

(III)

Mineral Acid →

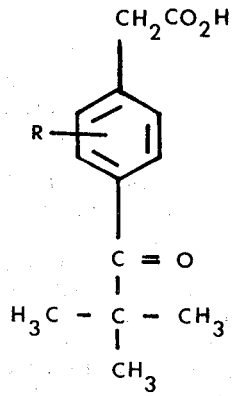

(IV)

where
R is as defined above.

The compounds of formula (IV) are prepared by hydrolyzing compounds of formula (III) with aqueous mineral acids. When R is hydrogen or halo, it is preferred that concentrated mineral acid be used. The acid can be hydrochloric acid, sulfuric acid, phosphoric acid and the like. The particular acid used is not critical but hydrochloric acid is preferred. The aqueous solvent can be water or a mixture of water and a water-soluble organic solvent, e.g., the lower alkanols. The preferred solvent is water, although the particular solvent used is not critical. The temperature of the reaction is also not critical, but it is preferred that the reaction be carried out at the reflux temperature of the solvent. For optimum results, the reaction is run for about 12 to 72 hours, preferably 40 to 50 hours. The product is recovered by conventional techniques, e.g., recrystallization.

Many of the compounds of formula (II) are known and may be prepared by methods disclosed in the literature. The compounds of formula (II) not specifically disclosed may be prepared from known starting materials by analogous methods.

The compounds of formula (IV) are useful as hypolipidemic agents as described in Belgian Pat. No. 803,686 issued Feb. 18, 1974. For use in treating lipidemia, satisfactory results are obtained when the compounds of formula (IV) are administered at a daily dosage of from about 1.0 milligrams to about 250 milligrams per kilogram of animal body weight. This daily dosage is preferably given in divided doses, e.g., 2 to 4 times a day, or in sustained release form. For most large mammals, the total daily dosage is from about 75 to 2500 milligrams, and dosage forms suitable for internal administration comprise from about 18.5 to about 1250 milligrams of the compound in admixture with a solid or liquid pharmaceutical carrier or diluent.

EXAMPLE 1

α-bromo-4-pivaloyl toluene.

To a flask equipped with stirrer, thermometer, condenser, addition funnel and heating mantle, there is added 44.0 grams (0.25 mole) of p-pivaloyl toluene at a temperature of 150°C. There is then added dropwise, while maintaining the temperature at 150°C., 40 grams (0.25 mole) of liquid bromine over a period of 10 to 15 minutes. The mixture is then stirred for an additional 10 minutes again while maintaining the temperature at about 140° to 150°C. The resulting brown liquid is cooled and degassed with nitrogen to obtain α-bromo-4-pivaloyl toluene in liquid form, b.p. 124° to 132°C. at 0.3 mm.

Following the above procedure and using in place of p-pivaloyl toluene an equivalent amount of
a. 2-chloro-4-pivaloyl toluene, or
b. 2-fluoro-4-pivaloyl toluene,
there is obtained
a. α-bromo-2-chloro-4-pivaloyl toluene, or
b. α-bromo-2-fluoro-4-pivaloyl toluene, respectively.

EXAMPLE 2

4-pivaloylphenyl acetonitrile.

A solution of 34.3 g. (0.700 mole) sodium cyanide in 40 ml. of water is warmed to 50°C. and a solution of α-bromo-4-pivaloyl toluene in 85 ml. ethanol is then added dropwise at such a rate as to maintain the temperature at 50°C. After the addition is complete, the mixture is refluxed for four hours. The excess ethanol is removed in vacuo and the resulting residue is treated with ether/water. The layers are separated and the ether is washed with cold 50% sulfuric acid, water and sodium bicarbonate; then the ether layer is dried over anhydrous magnesium sulfate, filtered and evaporated in vacuo. The residue is distilled in vacuo to give 4-pivaloylphenyl acetonitrile (b.p. 143°–148°C/0.75 mm $n^{22}=1.5244$.)

Following the above procedure and using in place of α-bromo-4-pivaloyl toluene an equivalent amount of
a. α-bromo-2-chloro-4-pivaloyl toluene, or
b. α-bromo-2-fluoro-4-pivaloyl toluene,
there is obtained
a. 2-chloro-4-pivaloylphenyl acetonitrile, or
b. 2-fluoro-4-pivaloylphenyl acetonitrile, respectively.

EXAMPLE 3

4-pivaloylphenyl acetic acid.

To a flask equipped with a stirrer, dropping funnel and condenser, there is added 50.0 g. (0.25 mole) 4-pivaloylphenyl acetonitrile to 1 liter concentrated hydrochloric acid which is then refluxed for 48 hours. The resultant precipitate is filtered, dissolved in chloroform, and washed with 2N sodium hydroxide. The basic aqueous phase is separated from the organic phase, cooled and acidified with concentrated hydrochloric acid and the resulting solid is then recrystallized from hot benzene to give 4-pivaloylphenyl acetic acid, m.p. 111°–112°C.

Following the above procedure and using in place of 4-pivaloylphenyl acetonitrile an equivalent amount of a. 2-chloro-4-pivaloylphenyl acetonitrile, or
b. 2-fluoro-4-pivaloylphenyl acetonitrile, there is obtained a. 2-chloro-4-pivaloylphenyl acetic acid, or
b. 2-fluoro-4-pivaloylphenyl acetic acid, respectively.

The above 4-pivaloylphenyl acetic acid is useful in the treatment of lipidemia when administered at a dosage of from about 50 to 250 milligrams four times per day.

What is claimed is:

1. An improved process for preparing a compound of the formula

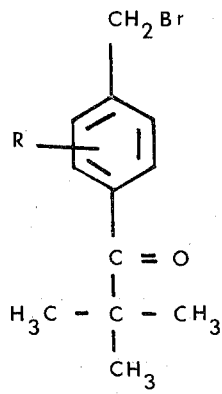

where
R represents hydrogen, halo having an atomic weight of about 19 to 36, which comprises adding liquid bromine to a compound of the formula

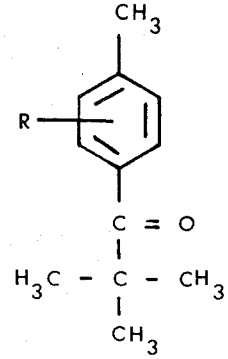

at a temperature of at least 100°C.

2. A process according to claim 1 which is carried out at a temperature of from about 108° to 175°C.

3. A process according to claim 1 which is carried out at a temperature of from about 115° to 150°C.

4. A process according to claim 1, in which the bromine is added over a period of 10 to 30 minutes.

5. A process according to claim 1, in which bromine is added dropwise to p-pivaloyl toluene at a mole ratio of 0.5–1:1.

* * * * *